United States Patent [19]
McKinney

[11] Patent Number: 5,167,665
[45] Date of Patent: Dec. 1, 1992

[54] METHOD OF ATTACHING OBJECTS TO BONE

[76] Inventor: William W. McKinney, 3208 Avondale, Fort Worth, Tex. 76109

[21] Appl. No.: 815,397

[22] Filed: Dec. 31, 1991

[51] Int. Cl.$^5$ .............................................. A61B 17/56
[52] U.S. Cl. ........................................ 606/75; 606/69
[58] Field of Search .................. 606/75, 72, 73, 95, 606/69, 70, 71; 411/481, 508–510, 923

[56] References Cited

U.S. PATENT DOCUMENTS

| | | | |
|---|---|---|---|
| 1,105,105 | 7/1914 | Sherman | 606/69 |
| 2,658,508 | 11/1953 | Gibson | 606/70 |
| 2,685,877 | 8/1954 | Dobelle | 128/92 |
| 2,745,308 | 5/1956 | Gisondi | 606/75 |
| 2,825,329 | 3/1958 | Caesar | 606/71 |
| 3,709,218 | 1/1973 | Halloran | 606/71 |
| 3,896,504 | 7/1975 | Fischer | 3/1.912 |
| 4,590,928 | 5/1986 | Hunt | 623/13 |
| 4,711,234 | 12/1968 | Vives | 411/446 |
| 4,776,328 | 10/1988 | Frey et al. | 128/92 |
| 4,790,304 | 12/1988 | Rosenberg | 623/18 |
| 4,988,351 | 1/1991 | Paulos | 606/75 |
| 5,013,316 | 5/1991 | Goble et al. | 606/72 |
| 5,037,422 | 8/1991 | Hayhurst et al. | 606/72 |

FOREIGN PATENT DOCUMENTS 8503857  9/1985  World Int. Prop. O. ............ 606/75

Primary Examiner—Robert A. Hafer
Assistant Examiner—Michael Brown
Attorney, Agent, or Firm—Geoffrey A. Mantooth

[57] ABSTRACT

An object is attached to a bone by using blind rivets. The blind rivets can be set from the outside of the bone. Each blind rivet has a body, with a head on one end, and a mandrel extending from the head end of the body. A hole is formed in the bone. The rivet is inserted through the object and into the bone through a hole in the bone cortex. The rivet is set by pulling on the mandrel with the rivet gun. The rivet secures the object to the proximal cortex layer of the bone. The method is used to attach objects such as plates and hip sockets to bone. In addition, the rivet can be provided with serrations on the head, wherein the rivet attaches soft tissue, such as muscle tendons, to bone.

8 Claims, 3 Drawing Sheets

METHOD OF ATTACHING OBJECTS TO BONE

FIELD OF THE INVENTION

The present invention relates to methods of attaching objects, such as plates, hip sockets and tissue, to bone.

BACKGROUND OF THE INVENTION

It is often necessary to attach objects to bone. For example, in repairing a fractured or damaged bone in a human being, the segments or fragments of bone must be fixated together to promote proper healing. Fixation may be accomplished by attaching a plate to the exterior of all of the bone segments.

Bone is made up of a hard exterior layer, known as the cortex, and soft interior tissue, known as cancellous bone or marrow. The cortex encompasses the entire outer surface of the bone. The cortex serves as a rigid, stable structure for attaching objects.

Prior art techniques utilize screws to secure a plate to a bone. To securely anchor a screw in the bone structure, bicortical placement of the screw in the bone is required. That is, the screw penetrates through the cortex layer that is adjacent to the object which is to be attached, then penetrates through the cancellous tissue in the interior of the bone and finally, penetrates into the opposite cortex layer on the other side of the bone. If the screw is not anchored into the opposite cortex layer, then the screw will wobble and will fail to securely couple the object to the bone.

Using screws in some situations increases the risk of the surgical procedure. For example, when fusing vertebrae together with a plate, the plate is coupled to the individual vertebra with screws. Each screw must extend through the anterior cortex, the cancellous tissue and into the posterior cortex. The tip of the screw must extend sufficiently far enough into the posterior cortex so as to be firmly anchored. However, the tip of the screw should not penetrate all the way through the thin posterior cortex because the spinal cord lies behind the posterior cortex. Any contact between the screw and the spinal cord would result in severe injury to the patient. The prior art relies on a ligament that is interposed between the posterior cortex and the spinal cord to provide some measure of safety by providing a space between the posterior cortex and the spinal cord. In addition, the prior art relies on the use of high resolution fluoroscopy to image the screw, wherein the surgeon can have an idea of where the tip of the screw is located. However, any improvement to this prior art procedure of attaching plates to vertebrae would no doubt be welcomed.

Another prior art technique of attaching objects to bone involves the use of toggle bolts. For example, in Fischer, U.S. Pat. No. 3,896,504, toggle bolts are used to secure a hip socket to bone. The installation of toggle bolts takes time and applies torque to the bone. In addition, once a toggle bolt is installed, removal is very difficult and time consuming. Removal is necessary, for example, if the toggle bolt is incorrectly installed.

SUMMARY OF THE INVENTION

It is therefore an object of the present invention to provide a method for attaching objects to bone, which method does not require bicortical placement of a fastener.

It is a further object of the present invention to provide a method for attaching objects to bone, which method allows a fastener to be removed from the bone.

The method of the present invention attaches an object to a bone in a patient. The bone has an exterior cortex and an interior cancellous region. The patient is entered to gain access to the bone. An area of the cortex is selected to which the object is to be attached. A hole is formed in the selected area of the cortex. The object is placed adjacent to the selected area of the cortex. There is provided rivet means with first and second ends, with the first end being larger than the second end. The rivet means second end is inserted through the object and into the hole in the cortex such that the first end abuts against the object. The rivet means second end is expanded against the cortex so as to secure the rivet means against the bone.

The method of the present invention allows an object to be quickly and easily attached to a bone. Blind rivets are utilized. Blind rivets allow a surgeon to insert a rivet and set the rivet from the same exterior location of the bone. To attach an object, the surgeon drills a hole in the bone cortex, places the object next to the bone and inserts the rivet through the object and into the bone. The rivet head abuts against the object, and a mandrel extends out away from the bone. A rivet gun is used to pull the mandrel and set the rivet. The mandrel snaps off the rivet after the rivet has been set. The rivet securely attaches the object to the cortical layer of the bone.

With the method of the present invention, an object can be attached to only one layer of the bone cortex. Thus, when fusing vertebrae together with a metal plate, the rivet does not penetrate the posterior cortex, thereby minimizing the risk of spinal cord injury. In addition, the method can be used to attach hip sockets to bone.

In one aspect, the rivet head is provided with gripping means. The rivet is used to attach soft tissue to bone, wherein the gripping means engages the soft tissue.

DESCRIPTION OF PREFERRED EMBODIMENT

Figure 1:
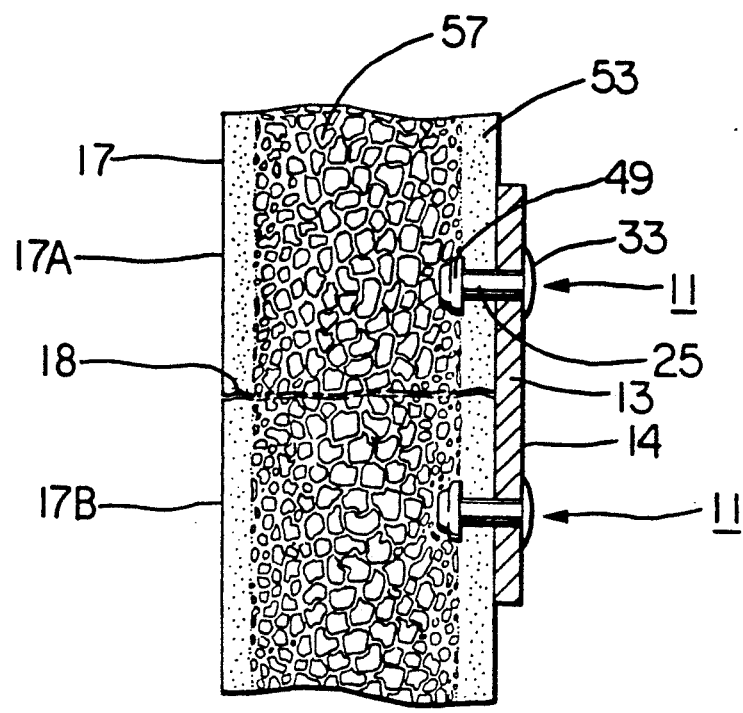
FIG. 1 is a schematic longitudinal cross-sectional view of a fractured bone, showing a metal plate coupled thereto with the method of the present invention, in accordance with a preferred embodiment.

Referring to FIG. 1, the method of the present invention is used during surgical procedures on animals or human beings to attach or couple objects, such as plates, hip sockets and tissue, to bone. The method of the present invention uses rivets 11 to attach an object 13 to bone 17. The rivets penetrate through the object to be attached and through the adjacent cortical layer of the bone. Specifically, the method uses blind rivets, wherein the rivets are installed from the exterior side of the cortical layer. Access to the interior of the bone to set the rivet is not required.

In FIG. 1 there is shown a schematic longitudinal cross-sectional view of a bone 17 and an object 13 that has been attached to the bone using the method of the present invention, in accordance with a preferred embodiment. The particular object shown in FIG. 1 is a metal plate 14. However, other type of objects can be attached to bone with the method of the present invention. The bone 17 has a cortex 53, which is the hard outer layer, and cancellous bone 57 or marrow, which is the soft tissue located inside of the cortex. The bone 17 that is shown in FIG. 1 is a long bone such as a human femur. The method of the present invention can be used to attach objects to other types of bone such as vertebrae and the ascetablum portion of the pelvis.

In the embodiment shown in FIG. 1, the bone 17 has a fracture 18 therethrough, which divides the bone into first and second segments 17A, 17B. The metal plate 14 extends across the fracture 18 and is attached to both the first and second segments 17A, 17B with the method of the present invention. The method uses the rivets 11 to attach the plate 14 to the bone 17.

Figure 3:
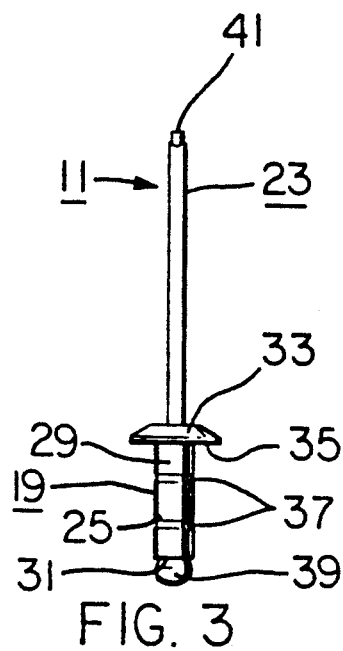
FIG. 3 is a side view of a rivet such as is used in the method of the present invention.

Referring to FIG. 3, the rivet 11 will now be described. The rivet is based on a conventional, commercially available blind rivet, also known as a "poprivet". While commercially available blind rivets are presumably made of aluminum, the blind rivets used in the present invention are of stainless steel or some other biocompatible material, which may be left in a human body for extended periods of time without adverse physiological consequences. The rivet is made of the same material as the object which is to be attached to avoid electrolysis. The rivet 11 includes a body 19 and a mandrel 23.

The rivet body 19 has a shank 25 and a head 33. The shank 25 is a cylindrical tube. The shank 25 has first and second ends 29, 31. The head 33 is integral with the first end 29 of the shank 25. The head 33 extends transversely out from the shank. The head 11 has an engaging surface 35 that faces the second end 31 of the shank. In the embodiment shown in FIG. 3, the engaging surface 35 is smooth and flat. The body 19 has an interior passage (not shown) extending from the shank second end 31 to the head 33. The interior passage receives the mandrel 23.

Figure 4:
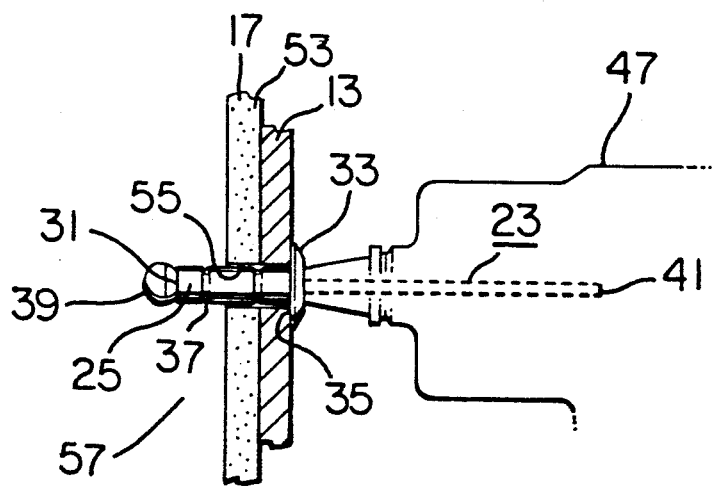
FIG. 4 is a schematic cross-sectional view of an object and the bone cortex, showing another step of the method of the present invention, wherein a rivet is inserted through the bone cortex.

In the embodiment shown in FIGS. 3 and 4, the rivet shank 19 has circumferential grooves 37 extending around the exterior surface of the shank. It is believed that the grooves 37 weaken the structure of the rivet shank 25 so as to control the flaring of the shank during the installation of the rivet.

The mandrel 23 is a shaft that extends through the body 19. One end of the mandrel has a bead 39 that is located adjacent to the shank second end 31. The bead 39 has a diameter that is larger than the inside diameter of the shank. The other end 41 of the mandrel 23 is free so as to be received by a rivet gun 47 (see FIG. 4). The body 19 is secured to the mandrel 23 so that sliding the body along the mandrel and rotating the body on the mandrel is difficult. The mandrel is believed to have a weakened portion located near the bead 39. This weakened portion allows the mandrel to separate from the bead and the body during installation of the rivet.

The rivet gun 47 receives the free end 41 of the mandrel (see FIG. 4). The rivet gun 47 is a conventional, commercially available gun that is used to install and set the blind rivet 11 shown in FIG. 3. The rivet gun 47 is pneumatic, being powered by compressed air. Compressed air is commonly available in surgical operating rooms. Alternatively, a manually operated conventional rivet tool can be used to set the rivet.

Figure 2:
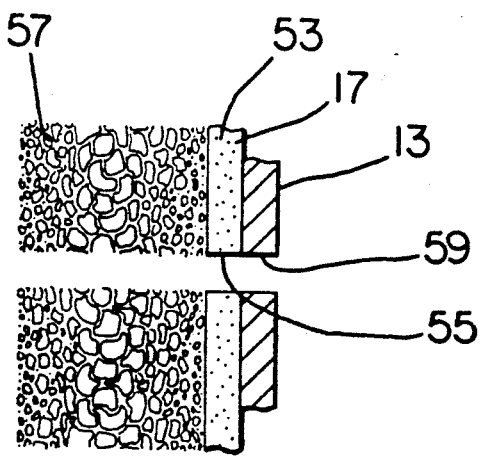
FIG. 2 is a schematic cross-sectional view of an object and a bone cortex, showing one step of the method of the present invention, wherein a hole is formed in the bone.

Referring to FIGS. 1-3, the method of the present invention will now be described. To attach an object 13 to a bone 17 with the rivets 11, the bone 17 must first be exposed by entering the patient in accordance with standard surgical procedures. After the bone 17 is exposed, an area of the bone is selected to which the object 13 is to be attached. The surgeon then selects the rivets 11 to be used. The surgeon selects the rivets based on their body lengths, body diameters, head diameter and separation force of the mandrel. Next, using a surgical drill, holes 55 (see FIG. 2) are drilled through the cortex 53 and into the cancellous tissue 57 at those locations where the surgeon intends to place the rivets. The diameter of each hole 55 is slightly larger than the outside diameter of the body shank 25, so that the rivet body 19 is easily inserted into the hole (see FIG. 4). The object 13 is typically provided with holes 59 for receiving the rivets. If no holes are provided in the object, then the surgeon can form the holes.

Next, the object is aligned over the bone so that the object holes 59 are aligned with the bone holes 55. Then, a rivet 11 is inserted into the rivet gun 47. The free end 41 of the mandrel is inserted into the rivet gun, as shown in FIG. 4. The gun 47 exerts a vacuum pull on the rivet 11 to prevent the rivet from falling out of the gun.

The surgeon inserts the rivet through the object hole 59 and the bone hole 55 so that the bead 39 is located in the cancellous tissue 57 and the rivet head 33 abuts against the object 13 (in FIG. 4, the cancellous tissue 57 is not shown for clarity). Then, the surgeon actuates the gun 47 to set the rivet. The gun 47 exerts a force on the mandrel 23 so as to pull the mandrel out of the bone. This force pulls the bead 39 toward the head 33 and causes the second end 31 of the shank 2 to collapse. As the shank second end 31 collapses, it increases in outside diameter to form an inner head 49 as shown in FIG. 1. When the inner head is formed, the mandrel 23 encounters resistance and separates from the bead, leaving the bead and the inner head 49 intact. The gun 47 pulls the mandrel 23 inside of the gun housing so that the surgeon does not have to be concerned with retrieving the mandrel. Thus, the mandrel 23 is removed from the patient.

Setting the rivet 11 with the gun 47 requires very little effort on the part of the surgeon. The surgeon merely pulls the trigger on the gun to actuate the gun 47. The rivet gun 47 does all the work in setting the rivet, with little kickback involved.

When the rivet 11 is set as shown in FIG. 1 the object 13 is clamped to the cortex 53 of the bone 17 by the two heads 33, 49 of the rivet. In addition, the portion of the shank 25 that is located inside of the holes 55, 59 expands against the bone and the object surrounding the holes.

The rivet 11 exerts a force on the cortex 53 during the formation of the inner head 49. The amount of force exerted depends on a number of variables such as the material used for the body 19, the wall thickness of the tubular shank 25 and the amount of force required to separate the mandrel 23 from the bead 39. The force exerted by the rivet on the cortex 53 can be reduced somewhat by positioning one of the grooves 37 slightly to the inside of the cortex, as shown in FIG. 4. The rivet 11 is selected so that the distance between the head 33 and one of the grooves 37 is slightly greater than the combined thickness of the object 13 and the cortex 53. It is believed that by positioning the groove 37 as described, the second end 31 of the shank flares out before contacting the cortex, thereby reducing the force on the cortex 53. The force exerted by the head 37 can be distributed over a larger area by inserting a washer on the shank and against the head. The washer effectively enlarges the head 33. The washer is made of stainless steel.

Although the rivet 11 has been described as being long enough to couple to a single cortex layer 53, namely the proximal cortex layer that is adjacent to the object 13, the method of the present invention allows objects to be coupled to both the proximal and the distal cortex layers. In this case, the rivet has a shank length such that the shank extends through the proximal cortex layer, the cancellous tissue and through the distal cortex layer, so that the bead 39 is positioned exteriorly of the bone. When the rivet is set, the head 33 is located adjacent to the object 13, while the other head 49 is located exteriorly of the distal cortex layer. Such an arrangement could be used when use of a long rivet extending all the way through a bone would cause no complications. Alternatively, a short rivet can be used, which rivet would not extend fully into the cancellous tissue from the proximal cortex layer. With a short rivet, the rivet is set by expanding against the bone surrounding the hole 55.

With the method of the present invention, the rivets can be removed, if necessary. The rivets can be removed, for example, to remove or replace an object from the bone. To remove a rivet, a surgical drill is used to drill the rivet out, in much the same way that a rivet is conventionally drilled out. The drill bores a hole through the head 33 and drills out the shank 25. The head 33 and the shank can then be removed. The inner head 49 is removed by enlarging the hole 55 in the cortex, wherein the inner head is removed through the enlarged hole.

The method of the present invention can be used to couple objects such as plates to bones. The plate is oriented so as to span the fracture site, as shown in FIG. 1. Then, plural rivets are installed on each side of the fracture site to firmly secure the plate to the bone segments. The plate fixates the bone segments 17A, 17B together.

Furthermore, the method of the present invention can be used to fuse vertebrae together with a plate. The plate spans across those vertebrae which are to be fused together. The plate is attached to the individual vertebrae with the rivets 11. Because no penetration of the posterior cortex of the vertebrae is required, the risk of injury to the spinal cord is minimized.

In addition, the method of the present invention can be used to attach prosthetic hip sockets to the ascetablum portion of the pelvic bone. A prosthetic hip socket is a cup designed to receive the hip ball located on top of the femur, or thigh bone. Thus, referring to FIG. 4, the object 13 would be the hip socket. The hip socket 13 is attached to the bone 17 with a single rivet in the center of the cup. The head of the rivet is countersunk into the hip socket so as to be flush with the surface of the hip socket. This avoids any interference by the rivet with the movement of the ball inside the socket.

Figure 5:
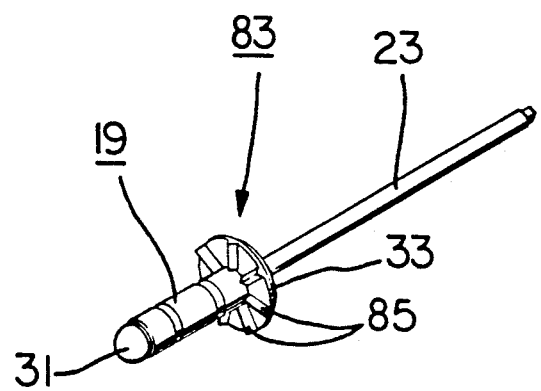
FIG. 5 is an isometric view of a rivet for use in attaching tissue to bone.
Figure 6:
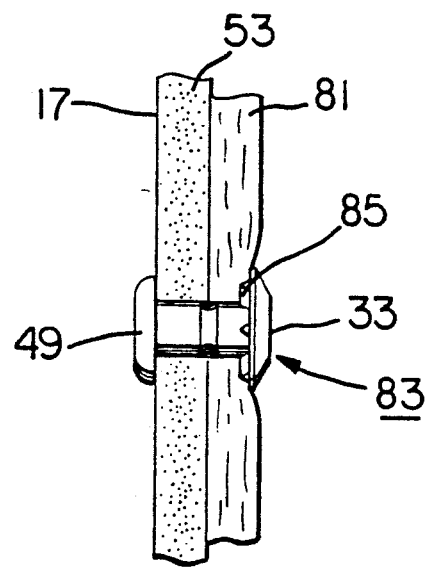
FIG. 6 is a schematic cross-sectional view showing the rivet of FIG. 5 attaching tissue to bone.

The method of the present invention can also be used to attach soft tissue 81, such as muscle tendons, to bone. Referring to FIGS. 5 and 6, a modified blind rivet 83 is shown attaching a muscle tendon 81 to a bone cortex 53. The rivet 83 has an enlarged head 85. The engaging surface 35 of the head has plural serrations 89 extending toward the second end 31. The serrations 89 serve as gripping means for allowing the rivet to more securely hold the muscle tendon 81. The rivet 83 is installed as described above. The surgeon forms a hole in the tendon 81 to allow the rivet 83 to be inserted therethrough.

The foregoing disclosure and the showings made in the drawings are merely illustrative of the principles of this invention and are not be interpreted in a limiting sense.

I claim:

1. A method of attaching an object to a bone in a patient, said bone having an exterior cortex and an interior cancellous region, comprising the steps of:
    a) entering said patient to gain access to said bone;
    b) selecting an area of said cortex to which an object is to be attached;
    c) forming a hole in said selected area of said cortex;
    d) placing said object adjacent to said selected area of said cortex;
    e) providing rivet means with first and second ends, said first end being larger than said second end;
    f) inserting said rivet means second end through said object and into said hole such that said first end abuts against said object;
    g) expanding said rivet means second end against said cortex so as to secure said rivet means against said bone.

2. A method of attaching an object to a bone in a patient, comprising the steps of:
    a) entering said patient to gain access to said bone;
    b) selecting an area of said cortex to which an object is to be attached, said selected area being a proximal cortex layer, said bone having a distal cortex layer that is separated from said proximal cortex layer by cancellous bone tissue, said proximal cortex layer having an interior side;
    c) forming a hole in said proximal cortex layer, said hole penetrating into said cancellous tissue;
    d) placing said object adjacent to said proximal cortex layer;
    e) selecting blind rivet means suitable for insertion into said hole, said rivet means being provided with first and second ends, said first end being larger than said second end;
    f) inserting said rivet means second end through said object and into said hole such that said first end abuts against said object;
    g) expanding said rivet means second end against said interior side of said proximal cortex layer so as to secure said rivet means against said bone.

3. The method of claim 2 wherein said step of expanding said rivet means second end comprises using pneumatic actuation means, said rivet means being provided with a mandrel for expanding said second end, said mandrel being pulled out of said hole by said pneumatic actuation means to expand said rivet means second end.

4. The method of claim 2 further comprising the step of removing said rivet means from said bone after said rivet means has been secured to said bone.

5. The method of claim 4 wherein said step of removing said rivet means comprises drilling through said rivet means.

6. The method of claim 2, wherein:
a) said step of selecting an area of said cortex comprises selecting an ascetablum region of a pelvic bone; and
b) said step of placing said object adjacent to said proximal cortex layer comprises placing a hip socket in said ascetablum.

7. The method of claim 2, wherein:
a) said step of selecting an area of said cortex comprises selecting a location in which to secure a plate;
b) said step of placing of said object adjacent to said proximal cortex layer comprises placing said plate across a site which is to be fixated by said plate.

8. A method of attaching soft tissue to a bone in a patient, comprising the steps of:
a) entering said patient to gain access to said bone;
b) selecting an area of said cortex to which said tissue is to be attached;
c) forming a hole in said selected area of said cortex;
d) placing said tissue adjacent to said selected area of cortex;
e) providing rivet means with first and second ends, said first end having a head, said head having an engaging surface that is provided with gripping means for gripping said tissue;
f) inserting said rivet means second end through said tissue and into said hole such that said head engaging surface and said gripping means contacts said tissue;
g) expanding said rivet means second end against said cortex so as to secure said rivet means against said bone with said tissue being interposed between said bone and said rivet means head, wherein said gripping means serves to secure said tissue.

* * * * *